United States Patent [19]

Batra

[11] Patent Number: 4,510,934

[45] Date of Patent: Apr. 16, 1985

[54] SUTURE

[76] Inventor: Subhash K. Batra, 3465 Leonard St., Raleigh, N.C. 27607

[21] Appl. No.: 494,243

[22] Filed: May 13, 1983

[51] Int. Cl.³ ............................................ A61L 17/00
[52] U.S. Cl. ................................. 128/335.5; 428/377
[58] Field of Search ........ 128/335.5, 334, 1, DIG. 14, 128/335, 339, 325, 326, 334 R, 334 C; 57/200, 210, 216, 224–226, 139; 3/36; 223/102; 604/164, 165; 428/377

[56] References Cited

U.S. PATENT DOCUMENTS 3,130,728 4/1964 Pearson et al. ................. 128/335.5
3,212,502 10/1965 Myers .................................. 128/339
4,372,293 2/1983 Vijil-Rosales .................... 128/335.5

Primary Examiner—C. Fred Rosenbaum
Assistant Examiner—Mario Costantino
Attorney, Agent, or Firm—Francis J. Bouda

[57] ABSTRACT

A surgical suture is described which consists of a monofilament core and a braided sheath surrounding the core. The sheath and the core are temporarily secured together at one end so that the core acts as a stiffener for the sheath during the surgical procedure. After the core and sheath are detached, the core is removed from the sheath and discarded, whereupon the sheath becomes flexible and easy to tie into a secure knot.

8 Claims, 7 Drawing Figures

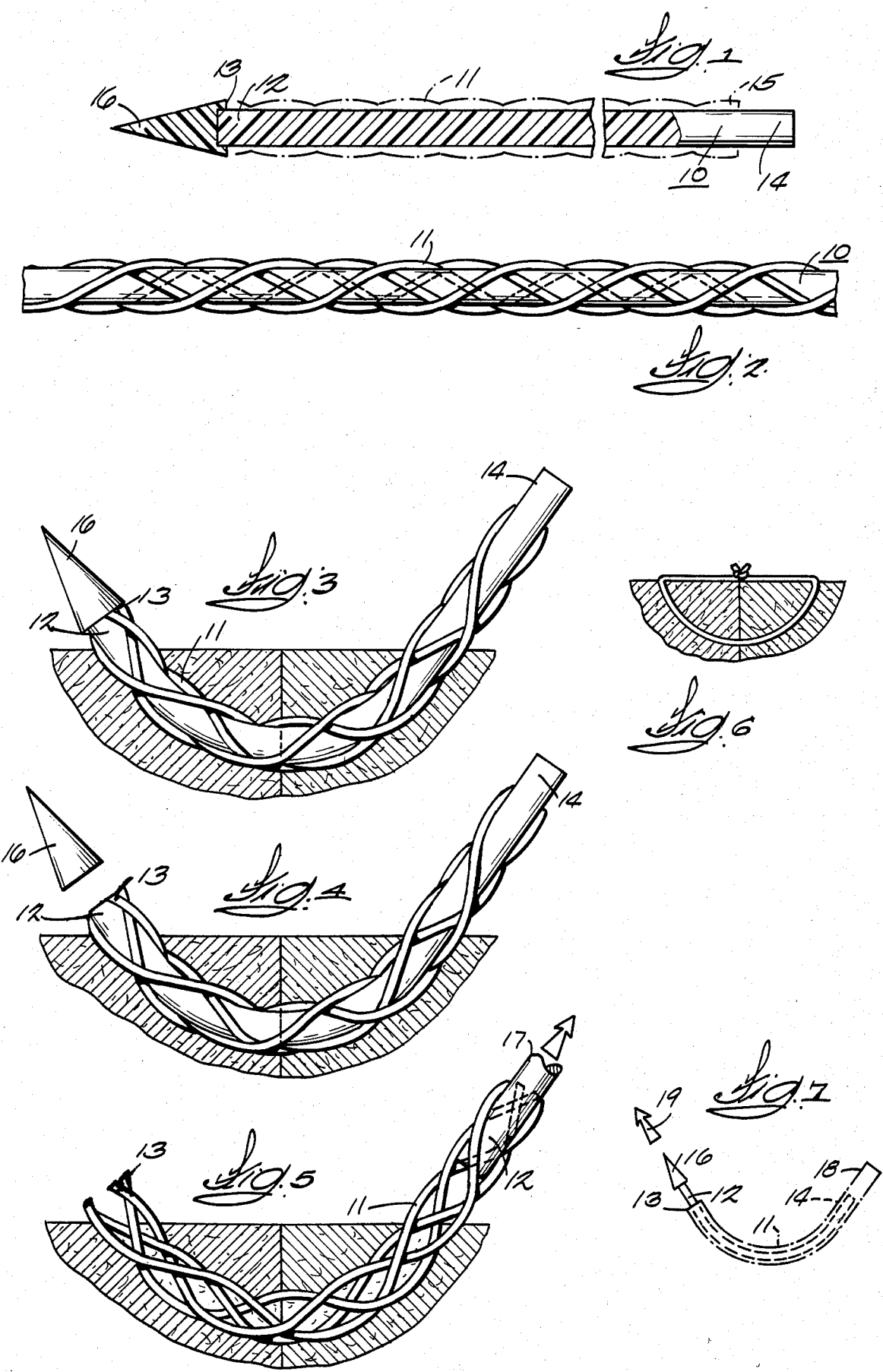

SUTURE

BACKGROUND OF THE INVENTION

Surgical threads or sutures have long been known in the art, and the medical profession has become accustomed to using gut or monofilament threads or sutures for sewing incisions or wounds. Such gut or monofilament threads have been well adapted to medical use, but have always had the disadvantage of being difficult to tie in a secure knot. This is the result of the bending stiffness to the gut or monofilament, but the very characteristic which makes it effective for threading through the eye of a surgical needle causes it to resist loop formation, and this relative stiffness in flexure contributes to the difficulty of forming a secure knot.

It has been well known in the textile art that braiding is an excellent means of converting several continuous filaments or yarns into a coherent linear yarn-like structure which translates, most efficiently, the strength potential of the constituents into the total strengths of the yarn-like structure.

Between the monofilaments and gut at one end of the spectrum, and braiding at the other end, there are a variety of twisted yarns, either single or multi-ply, which can be used to form a suture, but such twisted yarn, of comparable strength and coherence to the braided yarn, would be relatively stiff in flexure and would, like the monofilaments and gut, resist loop formation during knotting. Of these materials, the braided structures are usually tubular and are constructed so that the tightness of the braid can be controlled during formation.

Thus, though a braided structure would provide an excellent suture from the standpoint of tying a secure surgical knot, its inherent lack of stiffness prevents it from easy threading through a surgical needle, or for passing through the flesh.

Prior inventors have approached this problem in a number of different ways, and of relevance is the structure shown in Myers U.S. Pat. No. 3,212,502, wherein a monofilament is introduced into a tube, the tube fastened to a needle, and the tube plus needle used to draw the monofilament through the wound, whereafter the tube is removed and the monofilament left behind to do the tying.

The combination of a braided yarn and a monofilament for use in a surgical suture is also shown in Pearson U.S. Pat. No. 3,130,278, but in this case the braided portion and the monofilament are arranged in end-to-end relationship so that the braided portion is used to draw the monofilament into the flesh.

More recently, the Shalaby U.S. Pat. No. 4,105,034 discloses a structure wherein either braided or monofilament surgical sutures have tying characteristics improved by coating with certain chemicals.

SUMMARY OF THE INVENTION

The suture of the present invention utilizes the flexible characteristics of a braided material with the stiffening characteristics of a monofilament to provide a multi-element member which can be threaded easily through the wound and then separated, i.e., the monofilament portion separated from the braided portion, so that the monofilament is removed entirely from the wound area and the tying is done solely with the braided portion to provide a knot which is secure and the tightness of which can be controlled during the tying. Moreover, such a braided suture then does not resist loop formation during the tying of the knot, and because of its pliability (or flexibility), it handles excellently during tying and assists the surgeon during the performance of his surgical procedure. A knot made from such a braided tubular ribbon has greater surface utilization than a knot made from a twisted yarn or a monofilament of comparable strength and/or weight per unit length and, therefore, is much more secure.

Thus the suture of the present invention will be found to be uncomplicated and effective and will afford surgical material which is a better tool for the medical profession and increase the effectiveness of the doctor's performance.

Therefore, a principle object of the present invention is to provide a surgical suture which is stiff during the sewing operation, but which is flexible and easily knotted during the tying operation.

Another object of the present invention is to provide a multi-component suture consisting of a braided portion and a monofilament portion.

Another object of the present invention is to provide a suture which is stiff in flexure during insertion but which does not resist loop formation during subsequent tieing.

An additional object of the present invention is to provide a suture consisting of a braided sheath and a monofilament core which is unitary during the passage through the flesh but wherein the monofilament can be removed so that the tying is done only with the braided portion.

Yet another object of the present invention is to provide a braided tubular ribbon for a medical suture which has greater surface area during knotting than a knot made from twisted yarn or monofilament, and which will thus provide a more secure surgical knot.

With the above and other objects in view, more information and a better understanding of the present invention will be achieved by reference to the following detailed description.

DETAILED DESCRIPTION

For the purpose of illustrating the invention, there is shown in the accompanying drawings a form thereof which is at present preferred, although it is to be understood that the various instrumentalities of which the invention consists can be variously arranged and organized so that the invention is not limited to the precise arrangements and organizations of the instrumentalities as herein shown and described.

In the drawings wherein like reference characters indicate like parts:

FIG. 1 is a front elevational view, partly in section, of the suture of the present invention.

FIG. 2 is an enlarged, cross-sectional view of the combination braided and monofilament portion of the suture of the present invention.

FIG. 3 illustrates how the suture of the present invention is inserted in the flesh to close a wound.

FIG. 4 is similar to FIG. 3 illustrating how the tip or pointed end of the suture can be removed.

FIG. 5 is a view similar to FIGS. 3 and 4 showing how the monofilament is removed from the braided portion of the suture.

FIG. 6 is a view showing how the flexible, braided portion of the suture can be tied into a secure, surgical knot.

FIG. 7 is a view, similar to FIG. 5, of a modified form of the suture of the present invention.

In FIG. 1, I show a monofilament or gut member 10 which may be any of the well-known surgical monofilaments. Preferably it is a bio-compatible polymer, such as polyester, but such characteristic is not mandatory because the monofilament will ultimately be removed and not be left behind in the wound to remain in contact with the flesh.

As is characteristic of monofilaments, the material is relatively stiff, a feature which is to be avoided when the material is used to tie a secure knot. This anti-knotting characteristic of monofilaments has long been a problem for fishermen as well as surgeons.

Around the monofilament 10, a multi-strand braid 11 is formed. This braided portion may be made of a bio-compatible polymer, such as polyester, and the braiding around the monofilament core is performed much like the construction of electrical cables which have a braided cover around a solid wire.

Braiding is an excellent means of converting several continuous filaments or yarns into a coherent linear yarn-like structure, because it translates strength potential of the constituents into the strength of the yarn-like structure most efficiently.

A braided tightly-made around a monofilament core would collapse into a tubular ribbon when the core is removed, subsequent to formation, without losing the coherence or tightness of the structure. During the formation of the suture of the present invention, one end 12 of the monofilament 10 is secured to the braided portion 11, either by glueing or otherwise securing the portion in the area 13.

If the braid and the monofilament material are thermoplastic, the two end components of the structure can be fused together at each end to prevent fraying of the braid or separation of the core from the sheath. If needed or desirable, one end can be shaped as a conical, tapered, pointed tip during the process of fusion, simply by drawing slowly after heating. In some circumstances, the stiff conical end may, itself, serve as a threading needle, or in other cases a surgical needle may be clamped on to it. The tip may be straight, if desired, or may be curved as shown in FIGS. 3 and 4 so as to more easily pass through the flesh adjacent the wound.

Alternatively, though at one end the two components of the suture may be fused thermally (or otherwise glued), at the opposite end there may be an extra inch or more of the braided sheath (without the core) which could be threaded through the eye of a surgical needle. This is shown in FIG. 7.

In the preferred embodiment shown in FIGS. 1, 3, and 4, the end 14 of the monofilament 10, which extends beyond the end 15 of the braid 11, provides an end of the monofilament 10 which can be grasped by surgical forceps or the like.

Thus, after the stiff, curved end of the suture is passed through the flesh, as is shown in FIG. 3, the fused tip 16 may be cut off, as shown in FIG. 4, leaving the monofilament within the braided portion. Both components are within the flesh, but the monofilament is no longer secured to the braided portion.

When the surgeon grasps the severed end 17 of the braid, and pulls the free end 14 of the monofilament, the monofilament can be removed from the surgical area, leaving only the braided portion in place.

After the monofilament is removed and discarded, the braid can be knotted into one of the many secure, surgical knots as shown in FIG. 6.

In FIG. 7, there is shown a modified form of the suture of the present invention, wherein the sheath 11, at the end 18, extends beyond the end 14 of the core. The pointed end 16 is permanently fastened to the end 12 of the core, but is removably fastened to the end 13 of the sheath. In practice, after the suture is inserted into the flesh, and the pointed end 16 extends above the flesh, the pointed end 16 may be twisted or broken away from the end 13 of the sheath. The surgeon can then grasp the opposite end 18 of the sheath with one forceps and while pulling on the pointed end 16 with another pair of forceps, pull the core out of the sheath in the direction indicated by the arrow 19.

A braid tightly made around a monofilament core can collapse into a tubular ribbon when the core is removed, sub-sequent to formation, without losing the coherence or tightness of the structure. As a ribbon, it is very pliable or flexible and as a coherent, tightly-made ribbon, it handles excellently and flexibly during loop formation and subsequent knotting.

A knot made from tubular ribbon, and particular braided ribbon, involves much greater surface contact during knotting than a knot made from twisted yarn or monofilament of comparable strength and/or weight per unit length; and, therefore, it is much more secure.

As suggested earlier, braiding of the structure around a central core is not new, as is well known in the field of electrical cable construction. Moreover, as previously suggested, a combination of braided members and monofilament members has been suggested in the surgical-suture field. However, even where a combination of a tubular and a monofilament member has been suggested it is the monofilament which has remained in place for providing the mechanism to tie a knot and to hold the wound together. It has always been the tubular or braided member which has been discarded.

As can be clearly understood from the foregoing, the monfilament provides the stiffening member during the insertion through the flesh, and after releasing the monofilament from the braided member, it is the monofilament which is removed and discarded. Thus this braided structure, similar to a shoelace, has the advantage that it is strong and can be knotted securely in a non-slip configuration. But with the construction of the present invention, the flexible characteristic of a braided structure which makes it difficult to thread, because of its limpness, is overcome by providing the temporary and removable stiffening element, namely, the monofilament.

Although I have suggested that the materials be made of polyester, because of their bio-compatibility, economic availability and ease of fabrication, it is to be understood that any satisfactory material may be used for the braid or monofilament members as long as they can be temporarily combined to provide an initial stiffening characteristic and then subsequently separated so as to remove the stiff mono-filament and permit the flexible, braided member to be tied in a surgical knot.

It is to be understood that the present invention may be embodied in other specific forms without departing from the spirit or special attributes hereof, and it is therefore desired that the present embodiments be considered in all respects as illustrative, and therefore not restrictive, reference being made to the appended claims rather than to the foregoing description to indicate the scope of the invention.

Having thus described my invention, what I claim as new and desire to protect by Letters Patents are the following:

1. A surgical suture having
   a removable monofilament core extending the entire length of the suture, and
   a braided flexible sheath surrounding said core,
   said core and said sheath being separably fastened together at one end,
   said combination of core and sheath having sufficient stiffness to permit penetration of flesh, whereby said core is removed after penetration of flesh permitting tying of said sheath into a secure knot.

2. The suture of claim 1 wherein a pointed tip is formed at one end of said combination core and sheath.

3. The suture of claim 2 wherein said one end is formed into a curve.

4. The suture of claim 1 wherein said core extends beyond said sheath at the other end of said sheath.

5. The suture of claim 1 wherein said sheath is formed from a bio-compatible material.

6. The suture of claim 5 wherein said bio-compatible material is polyester.

7. The suture of claim 1 wherein said sheath extends beyond said core at the other end of said core.

8. The suture of claim 2 wherein said tip is formed by heat fusion of said sheath and said core.

* * * * *